United States Patent [19]

Hsu et al.

[11] Patent Number: 4,551,559
[45] Date of Patent: Nov. 5, 1985

[54] HYDROFORMYLATION CATALYST AND PROCESS

[75] Inventors: Chao-Yang Hsu, Media; Paul E. Ellis, Jr., Downingtown, both of Pa.

[73] Assignee: Sun Refining and Marketing Company, Philadelphia, Pa.

[21] Appl. No.: 732,314

[22] Filed: May 9, 1985

Related U.S. Application Data

[62] Division of Ser. No. 598,934, Apr. 11, 1984.

[51] Int. Cl.$^4$ .............................................. C07C 45/50
[52] U.S. Cl. ..................................... 568/454; 502/153
[58] Field of Search ......................... 502/153; 568/454

[56] References Cited

U.S. PATENT DOCUMENTS

| | | | |
|---|---|---|---|
| 3,876,672 | 4/1975 | Mrowca | 260/604 HF |
| 3,981,925 | 9/1976 | Schwager et al. | 568/454 |
| 3,996,293 | 12/1976 | Knifton et al. | 568/454 |
| 4,101,565 | 7/1978 | Poist | 568/454 |
| 4,155,939 | 5/1979 | Poist | 260/604 HF |
| 4,256,616 | 3/1981 | Hatanaka | 502/162 X |
| 4,370,258 | 1/1983 | Ogata et al. | 568/454 |
| 4,405,496 | 9/1983 | Hsu | 568/454 |

FOREIGN PATENT DOCUMENTS

| | | | |
|---|---|---|---|
| 56-118034 | 9/1981 | Japan | 502/162 |
| 57-134495 | 8/1982 | Japan | 502/162 |

OTHER PUBLICATIONS

Hsu et al "J. Amer. Chem. Soc." vol. 97, p. 3553, (1975).
Schwager et al "J. Cat." vol. 45, pp. 256–267, (1976).
Kawabata et al "J.C.S.Chem. Comm" pp. 462–463, (1979).
Kirk–Othmer *Encyclopedia of Chemical Technology*, (Third Edition) vol. 16, Pub. by John Wiley & Sons, N.Y. N.Y. pp. 637–653.

*Primary Examiner*—Werren B. Lone
*Attorney, Agent, or Firm*—J. Edward Hess; Donald R. Johnson; Stanford M. Back

[57] ABSTRACT

Olefins are hydroformylated with syngas in the presence of a novel organo metallic complex catalyst to form the corresponding aldehydes at high reaction rates and improved selectivity of linear aldehydes over branched aldehydes.

The novel catalyst comprises an organo metallic complex formed from a mixture of:
(1) platinum (II) acetylacetonate;
(2) a Group IVB metal halide; and
(3) a bidentate tertiary ligand of the formula

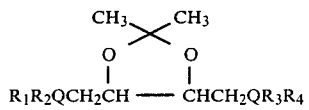

wherein Q is arsenic, antimony, or phosphorus; and $R_1$, $R_2$, $R_3$ and $R_4$ are alkyl, alkoxyl, aryl, or aryloxyl groups, and may be the same or different.

11 Claims, No Drawings

HYDROFORMYLATION CATALYST AND PROCESS

This is a division of application Ser. No. 598,934, filed Apr. 11, 1984.

BACKGROUND OF THE INVENTION

1. Scope of the Invention

This invention relates to the process of hydroformylating olefins with syngas in the presence of a novel catalyst composition to form aldehydes. More particularly, it relates to an improved olefin hydroformylation catalyst system comprising a mixture of platinum (II) and acetylacetonate; a Group IVB metal halide; and a bidentate tertiary ligand, each of which components is described in further detail below.

The novel organo metallic complex catalyst composition of this invention provides high reaction rates and high ratios of linear to branched aldehydes.

2. Description of the Prior Art

Processes of preparing aldehydes by hydroformylating an olefin with syngas, i.e., a mixture of hydrogen and carbon monoxide, in the presence of various catalysts, particularly cobalt and rhodium catalysts, is well known in the art. See, for example, Kirk-Othmer Encyclopedia of Chemical Technology ("OXO process"). Depending upon the catalyst, varying rates of reaction, and more importantly, different ratios of linear to branched aldehydes are obtained, the linear aldehydes being the preferred ones (as intermediates in the conversion, e.g., to alcohols by known hydrogenation methods and the like).

The use of platinum (II) complexes as hydroformylation catalysts in the OXO process, either alone, or in combination with $SnCl_2$, is known. Higher ratios of straight to branched aldehydes are obtained when tertiary phosphine-coordinated platinum complexes are used.

For example, $PtH(SnCl_3)(PPh_3)_2$ is shown by Hsu and Orchin, *J. Amer. Chem Soc.*, 97, 353 (1975) to be useful for conversion of 1-pentene to aldehydes. Schwager and Knifton, *J. Cat.*, 45, 256 (1976), U.S. Pat. No. 3,981,925 and U.S. Pat. No. 3,996,293 disclose use of $PtCl_2(PPh_3)_2 + SnCl_2$ for a similar reaction with 1-heptene. Kawabata, et al., *J.C.S. Chem. Comm*, 462 (1979) teach $Pt(PhCN)_2Cl_2 + Ph_2P(CH_2)_xPPh_2$ for conversion of 1-pentene to aldehydes. U.S. Pat. Nos. 4,101,565 and 4,155,939 show the dimer $(PtCl_2PPh_3)_2 + SnCl_2$ for hydroformylation of 1-hexene. U.S. Pat. No. 3,876,672 also shows hydroformylation of 1-hexene with $PtH(PPh_3)_3 + HSO_4^-$. See also, U.S. Pat. No. 4,405,496, which describes a platinum (acetylacetonate) in combination with a Group IVB metal halide and a tertiary phosphine. Also, U.S. Pat. No. 4,370,258 teaches the combination of platinum (II) complexed with phosphorus-, arsenic-, or antimony-containing bidentate ligands in combination with Group IVB metal halides, as hydroformylation catalysts. Other effective platinum (II) compounds include the ionic complexes shown in U.S. Pat. No. 3,876,672.

Generally speaking, however, it is recognized that platinum complex-based hydroformylation catalysts usually give slower reaction rates compared to those of the early cobalt and rhodium catalysts. It is, therefore, an object of this invention to provide an olefin hydroformylation catalyst which both gives faster reaction rates, and also maintains a high selectivity for linear over branched aldehydes.

SUMMARY OF INVENTION

In accordance with the present invention there is provided a novel olefin hydroformylation organic metallic catalyst system comprising:

(1) a platinum (II) acetylacetonate [$Pt(acac)_2$];

(2) a Group IVB metal halide of the type previously used in the art but which typically has one of the following formulas:

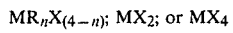

$MR_nX_{(4-n)}$; $MX_2$; or $MX_4$ wherein M is germanium, lead, or most preferably, tin; R is alkyl, aryl, alkoxyl, or aryloxyl, in which case n is an integer of from 1 to 3, or R is an anion derived from a diketone, diacid, or diester, in which case n is an integer of from 1 to 3 if the anion is a mono-anion, or n is 1 if the anion is a di-anion; and x is a halide, preferably chlorine; and (3) a bidentate tertiary ligand of the formula

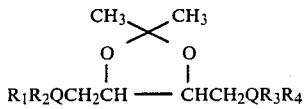

wherein Q is a Group VA metal, including arsenic, antimony, or preferably, phosphorus; and $R_1$, $R_2$, $R_3$ and $R_4$ are alkyl, aryl, alkoxyl, or aryloxyl groups, and may be the same or different.

In the above formulas the R groups desirably contain one to six carbon atoms when alkyl, such as methyl, ethyl, or hexyl; or six to twenty carbon atoms when aryl, such as phenyl, naphthyl, tolyl or the like. Alkyl and alkoxyl groups include cycloalkyl and cycloalkoxyl groups, while the aryl and aryloxyl groups include alkyl-substituted aromatic groups.

Also, the metal halides may include water of crystallization.

The invention is also directed the process of hydroformylating olefins with syngas in the presence of the aforedescribed catalysts to form aldehydes.

DESCRIPTION OF PREFERRED EMBODIMENTS OF THE CATALYST

The above-described catalyst of this invention is employed in a homogeneous system, the solvents for which may be selected from a wide range of solvents for the OXO reaction such as aromatic hydrocarbons, alkylaromatic hydrocarbons; alkyl, aryl, or alkylaryl ketones; or halogenated hydrocarbons. Illustrations of specific solvents include benzene, toluene, xylenes, ethylbenzene, tetralin, acetone, methylethyl ketone, acetophenone, dichloroethane, and the like.

The catalyst complexation may be accomplished separately, but is most conveniently prepared in situ by simply mixing together in the desired solvent the three aforesaid catalyst components, and thereafter carrying out the olefin hydroformylation process in a generally known manner. When combining these components, the ratios of the components, based on their metal content, are desirably in the range of about 0.5:1 to 20:1, and preferably less than 5:1 molar ratio for the [Group IVB metal]/[Pt]; and desirably in the range of from about 1:1 to 30:1, preferably less than 5:1 for the [P]/[Pt] molar ratio.

Although the reaction system is a homogeneous one, it has been found that the catalyst may readily be recovered and recycled with little or no loss of activity.

In addition to the Pt(acac)$_2$ component, the catalyst composition includes Group IVB metal halides of the formulas defined above. Examples of these compounds which may be used in forming the catalyst of this invention include:

diphenyl tin(IV)dichloride [Sn(C$_6$H$_5$)$_2$Cl$_2$],
tin(IV)dichlorodiacetylacetonate [Sn(acac)$_2$Cl$_2$],
tin(II)dichloride [SnCl$_2$.2H$_2$O or SnCl$_2$],
tin(IV)tetrachloride [SnCl$_4$], and
phenyltin(IV)trichloride [Sn(C$_6$H$_5$)Cl$_3$].

The third component of the catalyst complex, the bidentate tertiary ligand having the formula as defined above, include the following compounds:
2,3-o-isopropylidene-2,3-dihydroxy-1,4-bis(diphenylphosphino)butane ("DIOP"); 2,3-o-isopropylidene-2,3-dihydroxy-1,4-bis(di-p-tolylphosphino)butane; and 2,3-o-isopropylidene-2,3-dihydroxy-1,4-bis(di-o-tolylphosphino)butane.

Of these, DIOP, which can either be optically active, i.e., (+)DIOP or (−)DIOP, or optically inactive, as preferred.

Illustrations of preferred combinations of the above three components used to form the catalysts complex of this invention are set forth in the examples below.

DESCRIPTION OF THE PROCESS

The hydroformylation of olefins with syngas in the presence of a catalyst is generally well-known (see the cited prior art-supra), and need not be repeated in detail herein.

Suffice it to say that the olefin starting material may be any olefin known in the art which can be hydroformylated. Examples of such olefins include C$_2$-C$_{20}$ aliphatic or cycloaliphatic monolefins, and conjugated or non-conjugated aliphatic or cycloaliphatic diolefins which preferably are linear, but which may branched and/or substituted, including such substituted olefins as ethylenically unsaturated alcohols, aldehydes, ketones, esters and the like, as well as aromatic compounds whose ethylenically unsaturated side chain is capable of being hydroformylated, such as styrene or allylbenzene. Where mixtures of olefins are employed, the process of this invention nevertheless generally results in the selective formation of linear aldehydes in major yields.

The reaction conditions are those generally employed in the art, and may vary widely depending upon the olefin and catalyst employed, but which typically include temperatures of from about 25°–150° C., preferably 75°–105° C.; pressures of from about 100–3000 psi, preferably 750–1500 psi; and a syngas ratio of H$_2$/CO desirably in the range of from about 0.25 to 4 and more preferably 0.75 to 2.0 (molar ratio).

Finally, the concentration of catalyst complex employed in the reaction, based on the amount of metallic platinum in the complex, which may vary widely, is desirably in the range of from about $1 \times 10^{-5}$ to $1 \times 10^{-1}$ mole, and more preferably $1 \times 10^{-3}$ to $3 \times 10^{-2}$ mole, per mole of olefin present.

The hydroformylation process may be conducted in a batch, semicontinuous or continuous manner. Moreover, the process can be combined with hydrogenation of the aldehydes to alcohols by venting the reactor after aldehyde formation and introducing hydrogen under suitable conditions of temperature and pressure. The catalyst used for the hydroformylation can also be used for the hydrogenation or fresh catalyst can be added. Less preferably, the reactor is not vented and a large volume of hydrogen is introduced for admixture with syngas remaining from the hydroformylation.

The invention will now be illustrated by, but is not intended to be limited to, the following examples.

EXAMPLE 1

The following example demonstrates the employment of the catalyst of this invention in the hydroformylation of propylene to butyraldehyde.

An autoclave was charged under nitrogen atmosphere with 100 ml of p-xylene, 0.196 g (0.5 mmole) of Pt(acac)$_2$, 0.564 g (2.5 mmole) of SnCl$_2$.2H$_2$O, and 0.187 g (0.376 mmole) of DIOP. The autoclave was purged thoroughly with syngas (H$_2$/CO=1:1) then pressurized to 400 psig with syngas and stirred for 30 min. at ambient temperature. The contents of the autoclave were then quickly heated to 100° then 10.85 g (258 mmole) of propylene was added, whereupon the total pressure was adjusted to 1000 psig using a syngas reservoir. After 1 hr. of reaction, the autoclave was quickly cooled, and the liquid mixture was analyzed using vapor phase chromatography. Analytical data showed the yield of butyraldehyde to be 93% and the ratio of n-butyraldehyde to iso-butyraldehyde to be 4 to 1, corresponding to 80% of unbranched n-butyraldehyde. These results are shown in Table I.

EXAMPLES 2 TO 5

These examples, summarized in Table I, use the same procedure outlined in Example 1. The only change in each example is the amount of the bidentate diphosphine ligand, DIOP.

TABLE 1

|  | EXAMPLE 1 | EXAMPLE 2 | EXAMPLE 3 | EXAMPLE 4 | EXAMPLE 5 |
|---|---|---|---|---|---|
| REAGENTS |  |  |  |  |  |
| Propylene | 258 mmole | 254 mmole | 258 mmole | 253 mmole | 258 mmole |
| Pt(acac)$_2$ | 0.5 mmole | 0.5 mmole | 0.5 mmole | 0.5 mmole | 0.5 mmole |
| SnCl$_2$.2H$_2$O | 2.5 mmole | 2.5 mmole | 2.5 mmole | 2.5 mmole | 2.5 mmole |
| DIOP* | 0.38 mmole | 0.5 mmole | 0.63 mmole | 0.75 mmole | 0.88 mmole |
| p-xylene | 100 ml | 100 ml | 100 ml | 100 ml | 100 ml |
| H$_2$/CO (1:1) | 1000 psig | 1000 psig | 1000 psig | 1000 psig | 1000 psig |
| CONDITIONS |  |  |  |  |  |
| Temperature | 100° C. | 100° C. | 100° C. | 100° C. | 100° C. |
| Reaction Time | 1 hr. | 1 hr. | 1 hr. | 1 hr. | 1.5 hr. |
| RESULTS |  |  |  |  |  |
| Yield of C$_4$—Aldehydes | 93% | 97% | 90% | 41% | 10% |
| Ratio of n/iso-butyraldehyde | 80/20 | 80/20 | 80/20 | 82/18 | 84/16 |

TABLE 1-continued

|  | EXAMPLE 1 | EXAMPLE 2 | EXAMPLE 3 | EXAMPLE 4 | EXAMPLE 5 |
|---|---|---|---|---|---|
| Initial Rate** | 820 | 970 | 650 | 370 | 45 |

*DIOP = 2,3-o-isopropylene-2,3-dihydroxy-1,4-bis(diphenylphosphino)butane
**Initial Rate = mmoles $C_4$—aldehydes/mmole $Pt(acac)_2$/hr. based on first 20 min. of reaction.

EXAMPLE 6

In accordance with the procedures of Example 1, but substituting 1-butene for propylene, and 2,3-o-isopropylidene-2,3-dihydroxy-1,4-bis(di-p-tolylphosphino)butane for DIOP, there is obtained linear 1-pentanal in good yield and selectivity over the corresponding branched aldehyde.

In a like manner, but substituting 1-pentene for propylene, and $Sn(C_6H_5)_2Cl_2$ for $SnCl_2.2H_2O$, the corresponding linear 1-hexanal is obtained in good yield and selectivity.

EXAMPLE 7

In accordance with the procedure of Example 1, but substituting styrene for propylene, and 2,3-o-isopropylidene-2,3-dihydroxy-1,4-bis(di-o-tolylphosphino)butane for DIOP, there is obtained linear 3-phenylpropanal in good yield and selectivity over the corresponding branched aldehyde.

In a like manner, but substituting α-methylstyrene for propylene, and $Sn(C_6H_5)Cl_3$ for $SnCl_2.2H_2O$, the corresponding linear 3-phenylbutyraldehyde is obtained in good yield and selectivity.

EXAMPLE 8

In accordance with the procedures of Example 1, but substituting 2-pentene for propylene, and $SnC_4$ for $SnCl_2.2H_2O$, there is obtained linear 1-hexanal in good yield and selectivity over the corresponding branched aldehyde.

In a like manner, but substituting allylbenzene for propylene, there is obtained linear 4-phenylbutyraldehyde in good yields and selectivity.

EXAMPLE 9 (Prior Art)

This example illustrates the hydroformylation of propylene to butyraldehyde in the presence of a prior art platinum-phosphorus-tin complex catalyst in a manner similar to that disclosed in U.S. Pat. No. 3,981,925.

To a 300 ml stainless steel autoclave was added 100 ml of toluene as solvent, 0.53 g (1.0 mmole) of $PtCl_2(PPh_3)_2$, 1.14 g (5.0 mmole) of $SnCl_2.2H_2O$, and 1.31 g (5.0 mmole) of $PPh_3$. After the mixture was stirred for 15 minutes under a nitrogen atmosphere, the autoclave was purged with syngas ($H_2/CO=1:1$) and 10.5 g (250 mmole) of propylene was added. The autoclave was then charged with syngas ($H_2/CO=1:1$) to make a total pressure of 750 psig. After which the reactor was then quickly heated to 100° C. and the syngas pressure was maintained at 1000 psig through constant addition of syngas from a reservoir. After 4 hours of reaction, the autoclave was cooled to room temperature and the gas phase materials were vented. The liquid contents were removed and analyzed directly by vapor phase chromatography. Analysis of the reaction mixture indicated that 85% yield of butyraldehydes was obtained and the molar ratio of n-butyraldehydes to iso-butyraldehyde was 6.7 (i.e., 87% of normal aldehyde).

From a comparison of the results set forth in Table I with those of the above prior art example, it will be seen that significant improvements have been achieved in shortening the reaction time from about 4 hours down to about 1 hour when the catalyst of this invention is employed.

What we claim is:

1. In the process of hydroformylating an olefin having from about 2 to 20 carbon atoms by reacting the olefin with hydrogen and carbon monoxide at elevated pressures in the presence of a catalyst to produce an aldehyde, the improvement of using as the catalyst a catalyst system which comprises (1) a platinum (II) (acetylacetonate)$_2$; (2) a Group IVB metal halide; and (3) a bidentate tertiary ligand of the formula:

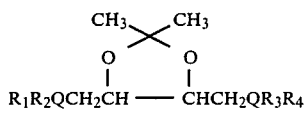

wherein Q is arsenic, antimony, or phosphorus; and $R_1$, $R_2$, $R_3$ and $R_4$ are alkyl, aryl, alkoxyl, or aryloxyl groups, and may be the same or different.

2. The process of claim 1 wherein the Group IVB metal halide is of the formula:

wherein M is germanium, lead, or tin; R is alkyl, aryl, alkoxyl, or aryloxy, in which case n is an integer of from 1 to 3, or R is an anion derived from a diketone, diacid, or diester, in which case n is an integer of from 1 to 3 if the anion is a mono-anion, or n is 1 if the anion is a di-anion; and X is a halide.

3. The process of claim 1 wherein the concentration of catalyst, based on the amount of metallic platinum in the complex, is from about $1 \times 10^{-5}$ to $1 \times 10^{-1}$ mole, per mole of olefin present.

4. The process of claim 1 wherein the molar ratio of the Group IVB metal to platinum is in the range of about 0.5:1 to 20:1 and the ratio of phosphorus to platinum is in the range of from about 1:1 to 30:1.

5. The process of claim 1 wherein the Group IVB metal halide is $SnCl_2$; and the bidentate tertiary ligand is 2,3-o-isopropylidene-2,3-dihydroxy-1,4-bis(diphenylphosphino)butane.

6. The process of claim 1 wherein the Group IVB metal halide is $Sn(C_6H_5)_2Cl_2$; and the bidentate tertiary ligand is 2,3-o-isopropylidene-2,3-dihydroxy-1,4-bis(diphenylphosphino)butane.

7. The process of claim 1 wherein the Group IVB metal halide is $Sn(acetylacetonate)_2Cl_2$; and the bidentate tertiary ligand is 2,3-o-isopropylidene-2,3-dihydroxy-1,4-bis(diphenylphosphino)butane.

8. The process of claim 1 wherein the Group IVB metal halide is $Sn(C_6H_5)Cl_3$; and the bidentate tertiary ligand is 2,3-o-isopropylidene-2,3-dihydroxy-1,4-bis(diphenylphosphino)butane.

9. The process of claim 1 wherein the Group IVB metal halide is $SnCl_2$; and the bidentate tertiary ligand is 2,3-o-isopropylidene-2,3-dihydroxy-1,4-bis(di-p-tolylphosphino)butane.

10. The process of claim 1 wherein the Group IVB metal halide is SnCl$_2$; and the bidentate tertiary ligand is 2,3-o-isopropylidene-2,3-dihydroxy-1,4-bis(di-o-tolylphosphino)butane.

11. The process of claim 1 wherein the olefin is propylene, 1-butene, 1-pentene, 2-pentene, styrene, α-methylstyrene, or allylbenzene.

* * * * *